(12) United States Patent
Garcia

(10) Patent No.: US 6,805,301 B2
(45) Date of Patent: Oct. 19, 2004

(54) FLUID PRODUCT DISPENSER

(75) Inventor: Firmin Garcia, Evreux (FR)

(73) Assignee: Valois S.A., Le Neubourg (FR)

( * ) Notice: Subject to any disclaimer, the term of this patent is extended or adjusted under 35 U.S.C. 154(b) by 360 days.

(21) Appl. No.: 10/067,018

(22) Filed: Feb. 4, 2002

(65) Prior Publication Data

US 2002/0104895 A1 Aug. 8, 2002

Related U.S. Application Data

(60) Provisional application No. 60/273,043, filed on Mar. 2, 2001.

(30) Foreign Application Priority Data

Feb. 7, 2001 (FR) .............................. 01 01620

(51) Int. Cl.$^7$ ................................ B05B 1/08
(52) U.S. Cl. ............................. 239/102.2; 239/102.1; 239/379; 239/552; 239/583; 239/596; 222/189.09; 128/200.16
(58) Field of Search ...................... 239/4, 102.1, 102.2, 239/302, 376, 379, 548, 552, 583, 585.1, 596; 128/200.14, 200.16, 200.21; 222/189.89

(56) References Cited

U.S. PATENT DOCUMENTS

| 3,648,929 | A | * | 3/1972 | Corbaz ..................... 239/102.2 |
| 4,093,124 | A | * | 6/1978 | Morane et al. ........ 222/189.09 |
| 4,702,418 | A | * | 10/1987 | Carter et al. .............. 239/102.2 |
| 4,882,096 | A | | 11/1989 | Rueben |
| 5,261,601 | A | * | 11/1993 | Ross et al. ................ 239/102.2 |
| 5,938,117 | A | * | 8/1999 | Ivri ................................ 239/4 |
| 6,152,383 | A | * | 11/2000 | Chen ....................... 239/102.2 |
| 6,601,581 | B1 | * | 8/2003 | Babaev .................. 128/200.16 |

FOREIGN PATENT DOCUMENTS

| DE | 23 23 489 | 9/1974 |
| DE | 32 02 597 A1 | 8/1983 |
| EP | 0 480 615 A1 | 4/1992 |
| JP | 03018292 | 8/1992 |
| WO | WO 00/40326 A1 | 7/2000 |

OTHER PUBLICATIONS

Rapport de Recherche Préliminaire in French priority patent application 01.01620, filed Feb. 7, 2001.

* cited by examiner

Primary Examiner—Steven J. Ganey
(74) Attorney, Agent, or Firm—Wood, Phillips, Katz, Clark & Mortimer

(57) ABSTRACT

A fluid product dispenser includes: a fluid product tank, a dispenser part comprising a pierced membrane connected directly to the tank, a mechanism to vibrate the pierced membrane, and an actuator button to activate the vibration mechanism. The tank is located above the pierced membrane such that the fluid product is supplied to the membrane from the tank using the force of gravity under normal operating conditions. The membrane is connected to the tank by a passage provided with an inlet valve capable of opening and cutting off the passage selectively.

7 Claims, 1 Drawing Sheet

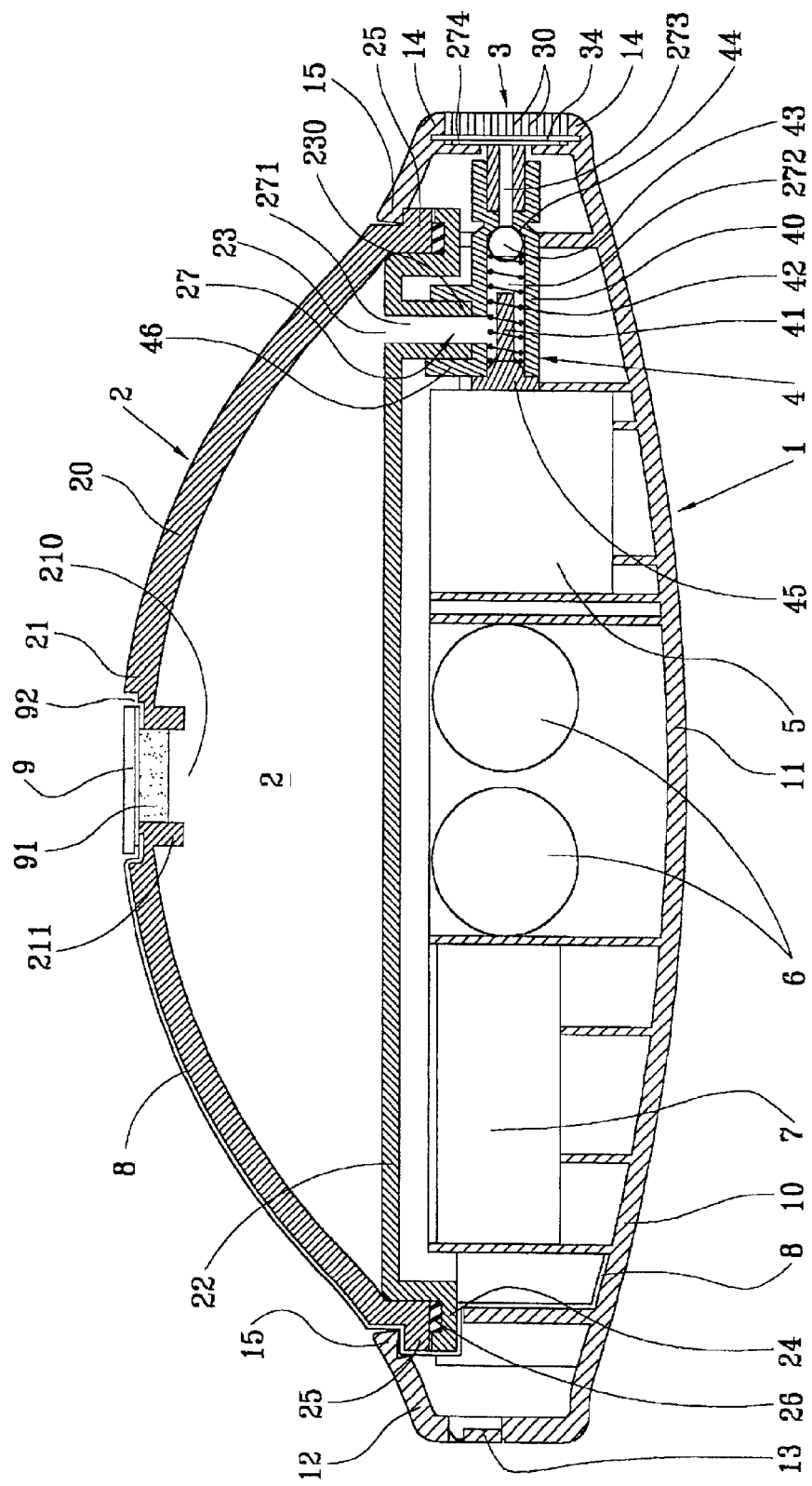
FIGURE UNIQUE

FLUID PRODUCT DISPENSER

This application claims the benefit under 35 U.S.C. §119(e) of U.S. provisional application Serial No. 60/273,043, filed Mar. 2, 2001, and priority under 35 U.S.C. §119(a)–(d) of French patent application No. FR-01.01620, filed Feb. 7, 2001.

TECHNICAL FIELD

The present invention relates to fluid product dispenser comprising a tank of fluid product and vibrating membrane that serves as a dispenser part. In general, the vibrating membrane is pierced with one or more dispenser holes through which the fluid product is dispensed under the effect of the vibration of the membrane. Means of vibration are generally provided in order to vibrate this pierced membrane: a piezoelectric part can constitute good vibration means to vibrate the membrane.

BACKGROUND OF THE INVENTION

The present invention relates more particularly to the cosmetics, perfume or pharmaceuticals sectors. The dispenser is therefore small enough to enable the user to take hold of it with a single hand. The user should also be able to actuate the dispenser with a single hand by pressing an actuator button intended to actuate the vibration means of the membrane.

In a standard pump that operates using suction and back-flow techniques, the pressure inside the tank does not act directly on the pump operation. A standard pump can operate with a tank that is pressurized or under vacuum, provided that excessive values are not reached. This is not the case with a pierced vibrating membrane that has neither an inlet nor an outlet valve. Consequently, the fluid product must be supplied to the vibrating membrane under pressure that is more or less equal to that of the atmosphere. A very slight vacuum or overpressure is, however, acceptable. If the tank is under pressure fluid product may leak through the holes in the pierced membrane, which would result in unacceptable seepage. On the other hand, a vacuum inside the tank would cause air to penetrate the dispenser through the holes of the pierced membrane. The spray would also be very poor quality.

In European Patents 0 615 470 and 0 696 234 fluid product dispensers are described that comprise a tank and a pierced membrane that vibrates by means of a piezoelectric part. Fluid supply means are provided that connect the tank to the membrane in order to supply the pierced membrane from the tank. As the pierced membrane is located above the tank under normal operating conditions it is necessary for the fluid to ascend against the force of gravity. In order for this to be possible, the supply means are capillary conduits in which the fluid products ascend naturally until they reach the pierced membrane.

However, it is not always easy to control the supply due to the fact that it uses capillarity.

BRIEF SUMMARY OF THE INVENTION

Consequently, the aim of the present invention is to overcome the above-mentioned drawbacks of the prior art due to capillarity by using another type of fluid-product supply from the tank to the vibrating membrane.

In order to achieve this, under normal operating conditions the tank is located above the pierced membrane such that the fluid product is supplied to the membrane from the tank using the force of gravity. The supply to the membrane therefore no longer depends on specific physical characteristics, i.e. capillarity, that cause the product to be dispensed at random. Gravity ensures that the membrane is directly and reliably supplied with fluid product under pressure that is more or less equal to that of the atmosphere. The term "under normal operating conditions" implies the period during which the button is actuated to activate the means of vibration. In other words, in the invention the tank is located above the membrane when the actuator button is depressed.

Advantageously, the dispenser includes a bottom that is intended to come into contact in the rest position with a surface that is more or less horizontal, the tank then being located above the vibrating membrane.

According to another advantageous characteristic, the membrane is connected to the tank by a passage provided with an inlet valve capable of opening and cutting off the passage selectively.

The vibration means and inlet valve are preferably electrically controlled. The inlet valve enables the membrane to be isolated from the tank such that said membrane is not subjected to any pressure. Any risk of the fluid product leaking or seeping through the holes of the pierced membrane is therefore avoided. Advantageously, the inlet valve only opens in periods during which the dispenser is actuated, i.e. when the actuator button is depressed. For example, the actuator button can activate the vibration means and open the inlet valve simultaneously. The pierced membrane is only therefore supplied with fluid product in the periods during which the dispenser is actuated.

According to another characteristic of the invention, the tank includes an upper section provided with an venting passage. Advantageously, the venting passage comprises a part made of porous material. The venting passage ensures that the pressure of the fluid product inside the tank is always more or less the same as atmospheric pressure. Furthermore, the passage is positioned at the top of the dispenser to prevent the fluid product from leaking through said passage.

According to another characteristic, the actuator button is located in the upper section of the tank and the venting passage is formed around said actuator button. The venting passage is also formed between the actuator button and the upper section of the tank. Advantageously, the actuator button masks the part made of a porous material. The actuator button is therefore used to both create and mask the venting passage.

BRIEF DESCRIPTION OF THE DRAWINGS

The invention will be better understood from the following detailed description. The description is of an embodiment of the invention given as a non-limitative example and refers to the attached single figure showing a vertical transversal section through a fluid product dispenser of the invention.

DETAILED DESCRIPTION

The dispenser comprises a base 1 onto which a tank 2 is mounted.

Base 1 constitutes a shell in two sections, 10 and 12, the peripheries of which are connected together by a clip system 13. The horizontal, transversal cross section of base 1 may be any shape, for example circular, elliptical or polygonal. The vertical cross section of the base is relatively flat and the lower shell section 10 comprises a bottom 11 on which the dispenser can stand such that it is stable. Base 1 comprises an aperture 14 in which a vibrating membrane 3 is housed. Aperture 14 can be located on the junction line between lower shell section 10 and upper shell section 12. Upper shell section 12 also constitutes a large aperture in which tank 2 is contained. In order to hold tank 2 in the aperture upper shell section 12 includes a retaining edge 15 capable of holding tank 2 onto base 1.

Base 1 also contains an inlet valve 4, an electromagnet 5, one or more batteries 6 and an electronic control system 7.

Tank 2 comprises a bottom 22 and a dome 20 the peripheries of which, 24 and 25 respectively, are connected together with a seal 26 which may be inserted between them to ensure leaktightness. Tank 2 thus created is held in the upper shell section 12 at peripheries 24, 25. Dome 20 comprises an upper section 21 that constitutes the top of the dome. According to the invention upper section 21 is provided with an aperture 210 formed by a small sleeve 211. A part made of porous material 91 is inserted into small sleeve 211 and blocks the passage while still letting air through. A venting passage is thus created through which the outside air may penetrate the inside of the tank as the fluid product is dispensed through pierced membrane 3. According to another characteristic of the invention an actuator button 9 is also provided on aperture 210 of upper section 21 of dome 20. The actuator button 9 may be a tactile contactor. Button 9 is located immediately above porous part 91 and, with small sleeve 211, defines a venting passage 92 that enables the outside air to come into contact with porous part 91. The venting passage is thus formed around button 9 and also masks porous part 91. It should also be noted that button 9 is ideally positioned facing bottom 11 on which the dispenser may stand on a more or less horizontal surface.

Button 9, which may be an electric switch, is connected to electronic control system 7 by a flat-track feed line 8 which may run around dome 20 and pass through base 1 through retaining edge 15. Therefore, depressing button 9 closes the electrical circuit and supplies the electronic control system.

Bottom 22 of tank 2 forms an outlet aperture 23 extended by a fluid product supply passage 27 that defines a first section of passage 271 directed downwards, slightly downstream of outlet aperture 23. This first section of passage 271 is defined by tubing 230 that is constituted by bottom 22 of the tank. Tubing 230 is also connected to a body of valve 40 that defines a connector sleeve 46 on tubing 230. Beyond first section of passage 271 the body of valve 40 defines a second section of passage 272 where an inlet valve 4 is constituted. Said inlet valve 4 is an electromagnetic valve comprising a ferromagnetic core 41 located in second section of passage 272, one end of which is blocked by a plug 45. Electromagnet 5 is located immediately behind plug 45 such that it can induce an electromagnetic field as far as ferromagnetic core 41. A valve ball 43, made of steel for example, is also held on a seat 44 constituted by body 4 by spring 42. Consequently, in the rest position, i.e. when there is no power supply to the electromagnet 5, ball 43 ensures the leaktightness of seat 44 and therefore isolates vibrating membrane 3 from tank 2. On the other hand, as soon as there is power supply to electromagnet 5 ferromagnetic core 41 becomes magnetic and draws valve ball 43 which then moves against the effect of spring 42 to be released from its seat 44 and creates a connection between second section of passage 272 and a subsequent section of passage 273 which is in direct contact with a gap 274 located in contact with the holes of passage 30 of pierced membrane 3.

According to the invention, pierced membrane 3 is supplied directly with fluid product from tank 2 due uniquely to the force of gravity when inlet valve 4 opens. The membrane may then be seen as being in direct contact with the fluid product from the tank because passage 27 can be considered a section or extension of the tank and therefore constitutes a part of the surface of the tank. Embodiments may be designed in which the membrane is located directly in the zone around the tank. In other words, the membrane is directly, continually and permanently connected to the tank when the valve is open. This is possible due to the fact that tank 2 is located above pierced membrane 3 when the dispenser is held in the position shown in the single figure, i.e. with the bottom directed downwards and the actuator button directed upwards. It is possible to supply fluid product using the force of gravity due to the direction of the supply passage 27, first section 271 of which extends downwards and sections 272 and 273 of which extend horizontally towards pierced membrane 3. To ensure that the device operates correctly, i.e. that there is a high quality of spray from pierced membrane 3, inlet valve 4 must be open in the periods during which the dispenser is actuated. On the other hand, it is advantageous for pierced membrane 3 to be isolated from tank 2 when the dispenser is in the rest position in order to avoid any leakage or seepage through holes 30 of pierced membrane 3. In a practical embodiment, button 9 can be used to switch on both the electronic control system of piezoelectric part 34 and electromagnet 5 simultaneously such that the valve opens at the same time as the product is sprayed through the membrane. When the valve is opened the passage creates direct, continuous contact from the tank to the pierced membrane that thus constitutes a part of the tank surface with its inner surface.

The invention enables a vibrating, pierced membrane to be supplied with fluid product from a tank under pressure approximately equal to that of the atmosphere and without the risk of the membrane leaking when the dispenser is in the rest position.

What is claimed is:

1. Fluid product dispenser comprising:

a fluid product tank, a dispenser part comprising a pierced membrane connected directly to the tank, vibration means to vibrate the pierced membrane, an actuator button to activate the vibration means, under normal operating conditions, the tank being located above the pierced membrane such that the fluid product is supplied to the membrane from the tank using the force of gravity, wherein the membrane is connected to the tank by a passage provided with an inlet valve capable of opening and cutting off the passage selectively, said inlet valve being opened when said vibration means are actuated.

2. Dispenser of claim 1 including a bottom that is intended to come into contact in the rest position with a surface that is more or less horizontal, the tank then being located above the vibrating membrane.

3. Dispenser of claim 1, wherein the vibration means and inlet valve are electrically controlled.

4. Fluid product dispenser comprising:

a fluid product tank, a dispenser part comprising a pierced membrane connected directly to the tank, vibration means to vibrate the pierced membrane, an actuator button to activate the vibration means, under normal operating conditions, the tank being located above the pierced membrane such that the fluid product is supplied to the membrane from the tank using the force of gravity, wherein the tank comprises an upper section located at the top of and above the level of the fluid product, said upper section being provided with a venting passage.

5. Dispenser of claim 4, wherein the venting passage comprises a part made of a porous material.

6. Fluid product dispenser comprising:

a fluid product tank, a dispenser part comprising a pierced membrane connected directly to the tank, vibration means to vibrate the pierced membrane, an actuator button to activate the vibration means, under normal operating conditions, the tank being located above the pierced membrane such that the fluid product is supplied to the membrane from the tank using the force of gravity, wherein the tank comprises an upper section provided with a venting passage comprising a part made of a porous material, and wherein the actuator button masks the part made of a porous material.

7. Fluid product dispenser comprising:

a fluid product tank, a dispenser part comprising a pierced membrane connected directly to the tank, vibration means to vibrate the pierced membrane, an actuator button to activate the vibration means, under normal operating conditions, the tank being located above the pierced membrane such that the fluid product is supplied to the membrane from the tank using the force of gravity, wherein the tank comprises an upper section provided with a venting passage, and wherein the actuator button is located in the upper section of the tank, the venting passage being formed around the actuator button between the actuator button and the upper section of the tank.

* * * * *